(12) United States Patent
Otto

(10) Patent No.: US 8,912,899 B2
(45) Date of Patent: Dec. 16, 2014

(54) WIRELESS SENSOR NETWORK CALIBRATION SYSTEM AND METHOD

(75) Inventor: Chris A. Otto, Huntsville, AL (US)

(73) Assignee: Integrity Tracking, LLC, Boca Raton, FL (US)

( * ) Notice: Subject to any disclaimer, the term of this patent is extended or adjusted under 35 U.S.C. 154(b) by 553 days.

(21) Appl. No.: 11/972,197

(22) Filed: Jan. 10, 2008

(65) Prior Publication Data

US 2008/0211657 A1    Sep. 4, 2008

Related U.S. Application Data

(60) Provisional application No. 60/884,352, filed on Jan. 10, 2007.

(51) Int. Cl.
| | |
|---|---|
| *G08B 1/08* | (2006.01) |
| *A61B 5/00* | (2006.01) |
| *G08B 25/10* | (2006.01) |
| *A61B 5/145* | (2006.01) |
| *A61B 5/0205* | (2006.01) |

(52) U.S. Cl.
CPC .............. *G08B 25/10* (2013.01); *A61B 5/0024* (2013.01); *A61B 5/0002* (2013.01); *A61B 5/145* (2013.01); *A61B 2562/0219* (2013.01); *A61B 5/0205* (2013.01); *A61B 5/02055* (2013.01)
USPC .............. 340/539.12; 340/539.1; 340/539.11; 702/85; 702/94; 702/96; 600/595

(58) Field of Classification Search
CPC .... A61B 5/0002; A61B 5/0031; A61B 5/021; G06F 19/3418; G06Q 50/22
USPC ............ 340/539.12, 500, 531, 539.1, 539.11, 340/286.01, 286.02, 540, 501; 702/1, 85, 702/91, 92, 94, 99, 104, 127, 130, 131, 136, 702/139, 145; 600/595
See application file for complete search history.

(56) References Cited

U.S. PATENT DOCUMENTS

| | | | | |
|---|---|---|---|---|
| 5,221,088 | A * | 6/1993 | McTeigue et al. | 473/201 |
| 5,372,365 | A * | 12/1994 | McTeigue et al. | 473/409 |
| 5,440,135 | A * | 8/1995 | Shonka | 250/374 |
| 5,959,529 | A * | 9/1999 | Kail, IV | 340/539.12 |
| 6,160,478 | A | 12/2000 | Jacobsen et al. | |

(Continued)

FOREIGN PATENT DOCUMENTS

WO    WO2006/064397 A2    6/2006

OTHER PUBLICATIONS

Jovanov, Emil et al., A Wireless Body Area Network of Intelligent Motion Sensors for Computer Assisted Physical Rehabilitation, Journal of NeuroEngineering and Rehabilitation, Rochester, MN, Mar. 2005.

(Continued)

*Primary Examiner* — Steven Lim
*Assistant Examiner* — Sisay Yacob
(74) *Attorney, Agent, or Firm* — Ann I. Dennen; Lanier Ford Shaver & Payne P.C.

(57) ABSTRACT

A system has at least one sensor and a controller communicatively coupled to the sensor. The system further has logic configured to calculate a calibration value based upon an initial state of the sensor and store the calibration value in memory.

19 Claims, 13 Drawing Sheets

(56) References Cited

U.S. PATENT DOCUMENTS

| | | |
|---|---|---|
| 6,198,394 B1 | 3/2001 | Jacobsen et al. |
| 6,474,159 B1* | 11/2002 | Foxlin et al. ............... 73/488 |
| 6,609,076 B2* | 8/2003 | Schuh et al. ................ 702/99 |
| 6,823,279 B1* | 11/2004 | Nadkarni et al. ............ 702/104 |
| 7,211,053 B2 | 5/2007 | Marmaropoulos et al. |
| 2003/0215130 A1* | 11/2003 | Nakamura et al. ............ 382/154 |
| 2004/0017210 A1* | 1/2004 | Johnson et al. .............. 324/661 |
| 2004/0027246 A1 | 2/2004 | Aguglia |
| 2004/0059205 A1 | 3/2004 | Carlson et al. |
| 2004/0077934 A1 | 4/2004 | Massad |
| 2004/0116822 A1 | 6/2004 | Lindsey |
| 2004/0199056 A1 | 10/2004 | Husemann et al. |
| 2006/0031102 A1 | 2/2006 | Teller et al. |
| 2006/0161363 A1* | 7/2006 | Shibasaki et al. ............. 702/94 |
| 2006/0238333 A1 | 10/2006 | Welch et al. |
| 2007/0038268 A1* | 2/2007 | Weinberg et al. ............. 607/62 |
| 2007/0043304 A1 | 2/2007 | Katayama |
| 2007/0063850 A1 | 3/2007 | Devaul et al. |
| 2007/0209669 A1 | 9/2007 | Derchak |
| 2007/0219059 A1 | 9/2007 | Schwartz et al. |
| 2007/0239229 A1 | 10/2007 | Masoud et al. |
| 2007/0250286 A1 | 10/2007 | Duncan et al. |
| 2007/0276270 A1 | 11/2007 | Tran |

OTHER PUBLICATIONS

Kouvatsos, D. D. et al, Performance Issues in a Secure Health Monitoring Wireless Sensor Network, University of Bradford, Bradford, UK.

Christian, Andrew et al., Gathering Motion Data Using Featherweight Sensors and TCP/IP over 802.15.4, Cambridge Research Laboratory, IEEE International Symposium on Wearable Computing, Workshop on On-Body Sensing, Osaka, JP, Oct. 2005.

Lo, Benny P. L. et al., Body Sensor Network—A Wireless Sensor Platform for Pervasive Healthcare Monitoring, Imperial College, London, UK.

Jovanov, Emil, Wireless Technology and System Integration in Body Area Networks for m-Health Applications, University of Alabama in Huntsville, Huntsville, AL.

\* cited by examiner

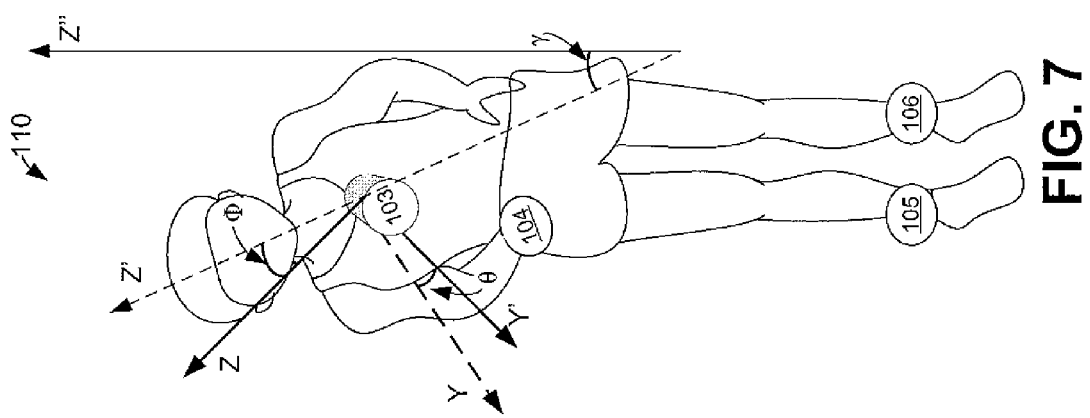

WIRELESS SENSOR NETWORK CALIBRATION SYSTEM AND METHOD

CROSS REFERENCE TO RELATED APPLICATION

This application claims priority to U.S. Provisional Application No. 60/884,352, entitled "Wireless Sensor Network System and Method for Using the Same," filed on Jan. 10, 2007, which is incorporated herein by reference.

FIELD OF THE INVENTION

The present invention relates generally to the field of wireless sensor networks. In particular, the present invention relates to wireless sensor networks which monitor one or more external signals wherein a change in such signals triggers detection, monitoring, recording, and reporting functions of the system. More particularly, the present invention relates to a wireless sensor network system to be used for physiological health monitoring, environmental monitoring, industrial applications, machinery maintenance, and other complex networking environments.

BACKGROUND OF THE INVENTION

Wireless sensor networks are known in the field of computing. Such networks are used for detecting, monitoring, recording, and reporting signal changes specific to the application in which it is used. For example, in a physiological health monitoring application, a wireless sensor network may include accelerometer sensors for measuring motion and orientation; temperature and humidity sensors; electrodes and bio-amplifiers for measuring heart waveforms, respiration, and muscle activity; oxygen saturation ($SPO_2$) sensors; and galvanic skin response (GSR) sensors.

Wireless sensor networks are composed of one or more sensor nodes and a system controller. Sensor nodes include a computing platform with wireless communication capabilities and one or more sensor devices. The system controller provides a data sync point for the collection and extraction of data, system configuration capabilities, and may include an interface for the end user of the wireless sensor network. The system controller may be referred to as a personal server, network coordinator, or personal area network (PAN) coordinator. The system controller may provide visual, audible or other signals to the user in response to certain events.

"Events" refer to specific changes in signals such as heartbeat detection and health monitoring applications, temperature detection and environmental monitoring, or vibration at specified frequencies in industrial applications. Events can also be used to describe and extract complex features which require combining and analyzing results from multiple signals and sensors.

In resource constrained systems such as wireless sensor networks, nodes are battery powered, placing a premium on low power consumption. Furthermore, such nodes are often manufactured with unique identifiers, making placement of such nodes throughout the network in its desired application critical to its proper function in the system. Furthermore, a wireless sensor network may contain a plurality of sensor nodes, each producing various types of data, each requiring a different amount of power consumption and memory, and any of which may be important to the overall understanding of the system in which it is operating.

Prior art wireless sensor networks rely on complex central monitoring units and require complex signal processing in order to effectively manage data generated by the sensor nodes. It is desirable, therefore, to provide a wireless sensor network capable of reserving memory, controlling the delivery of contextual event data, and allowing for node discovery, configuration, and calibration in multi-node applications. Each of these capabilities is provided in the present invention.

SUMMARY OF THE INVENTION

The present disclosure is directed to a wireless sensor network capable of event management and memory conservation, contextual event data delivery, and node discovery configuration and calibration in multi-node applications.

A system in accordance with an embodiment of the present disclosure has at least one sensor and a controller communicatively coupled to the sensor. The system further has logic configured to calculate a calibration value based upon an initial state of the sensor and store the calibration value in memory.

A method in accordance with an embodiment of the present disclosure can be generally conceptualized by the following steps: 1) coupling a sensor to a body; communicatively coupling a controller to the sensor; and calculating a calibration value based upon an initial state of the sensor.

BRIEF DESCRIPTION OF THE DRAWINGS

The present invention is described with reference to the accompanying drawings.

FIG. 7 is a drawing of a user's axes and the effect of the user's movement as used by a calibration function of the system depicted in FIG. 1.

DETAILED DESCRIPTION

Figure 1:
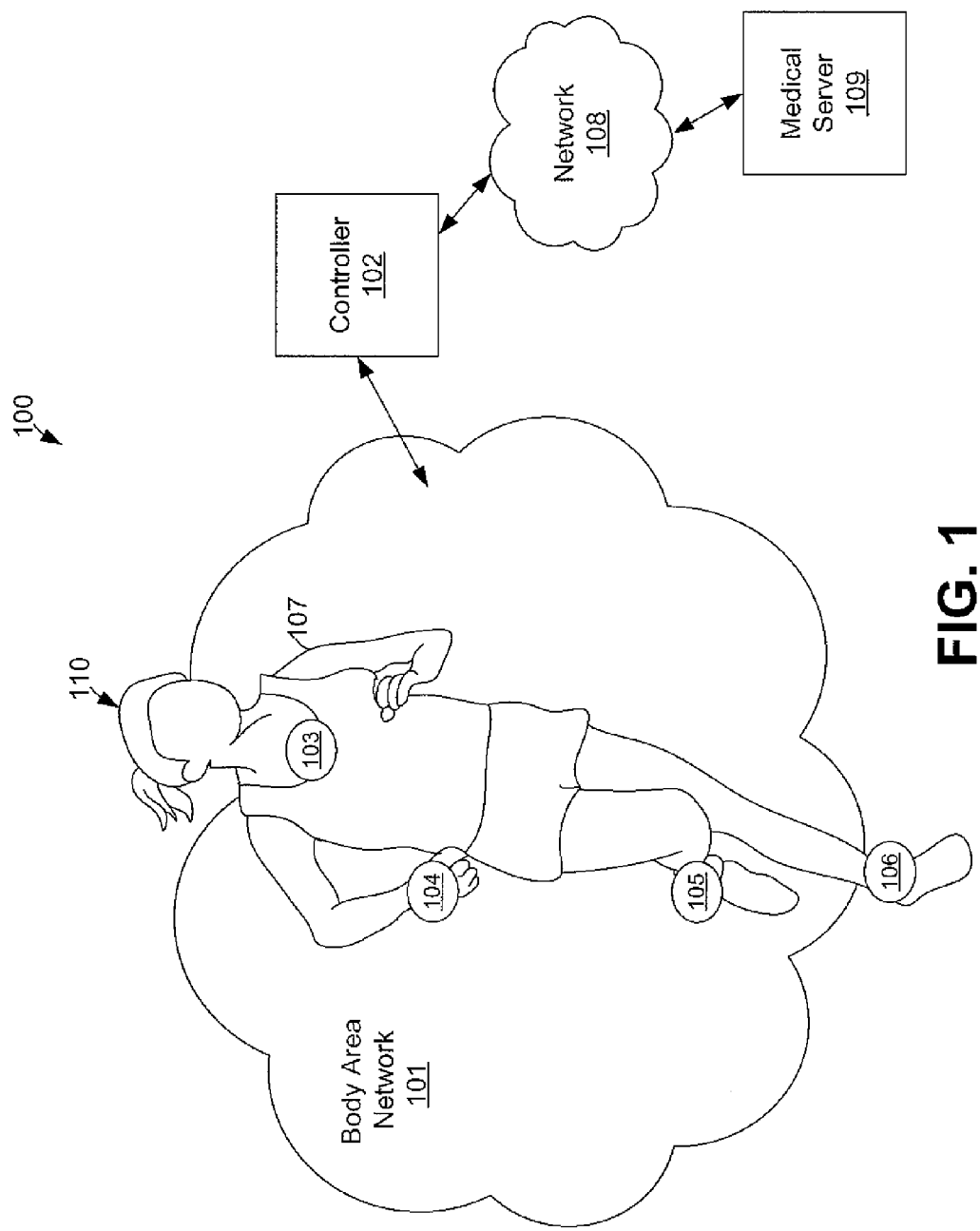
FIG. 1 depicts a wireless sensor network system in accordance with an embodiment of the present disclosure.

FIG. 1 depicts a wireless sensor network system 100 in accordance with an embodiment of the present disclosure.

The system 100 comprises a plurality of sensors 103-106 coupled to a body 107 of a user 110. In addition, the system 100 comprises a controller 102 that is communicatively coupled to the sensors 103-107 via a body area network 101.

In one embodiment, the functional capabilities and the hardware (not shown) of the sensors 103-106 are characteristically homogenous. In another embodiment, the functional and hardware characteristics of each of the sensors 103-106 may differ. The sensors 103-106 include, for example, one or more accelerometer sensors for measuring motion and orientation, temperature and humidity sensors, electrodes and bio-amplifiers for measuring heart rate and heart waveforms, humidity sensors, respiration sensors, muscle activity sensors, $SpO_2$ sensors, and/or GSRs. These types of sensors are identified for exemplary purposes, and other types of sensors can be used in other embodiments of the wireless sensor network system 100.

Furthermore, four sensors 103-106 are shown coupled to the user's body 107 in FIG. 1. However, four is an exemplary and arbitrary number. More or fewer sensors 103-106 may be used in other embodiments of the wireless sensor network system 100.

As indicated hereinabove, the controller 102 is communicatively and wirelessly coupled to the plurality of sensors 103-106 through the body area network 101. The controller 102 performs certain initial functions, including discovery of available sensors 103-106, configuration of the sensors 103-106, and calibration of the system 100 related to orientation of the user's body 107. Note that the controller 102 may be, for example, a smart phone, an intelligent wrist watch, or a desktop appliance, such as a wireless gateway. Further note that a "smart phone" refers to a telephone that has data accessing features. As an example, a mobile telephone that has voice services in combination with Internet, e-mail, fax, and/or pager capabilities is referred to as a smart phone.

Once the controller 102 has performed the initial functions, the controller 102 receives data from the plurality of sensors 103-106 related to the physical and physiological aspects of the body 107 through the body area network 101. The data may be indicative, for example, of the present orientation of the body 107, the heartbeat waveform, humidity, oxygen saturation, muscle activity, and/or temperature.

Furthermore, the controller 102 may communicate audibly or visually information related to the sensors 103-106 to the user 110. For example, during the initial functions, the controller 102 may communicate commands to the user 110 related to placement of the sensors 103-106 on the user's body 107. The initial functions of discovery, configuration, and calibration are described further herein.

The controller 102 may be, for example, a hand-held device like a personal digital assistant (PDA) or any other type of device capable of communicating over the body area network 101 with the sensors 103-106. Accordingly, the controller 102 comprises software, hardware, or a combination thereof to perform a variety of functions. Such functions may include, for example, wireless communications, network access, or the like. The controller 102 may be stylus-driven, keyboard driven, or voice driven. Alternatively, the controller 102 may be a personal computer that communicates wirelessly with the sensors 103-106. The controller 102 is described further with reference to FIG. 2.

The body area network 101 may be any type of body area network known in the art or future-developed. In one embodiment, the body area network 101 is implemented with Zigbee®. "Zigbee" refers a set of specifications for communication protocols for digital radios built around the Institute of Electrical and Electronic Engineers (IEEE) standard 802.15.4 wireless protocol.

In another embodiment, the body area network 101 is implemented with Bluetooth®. "Bluetooth" refers to another set of specifications for communication protocols for a personal area networks (PAN). Note that Zigbee and Bluetooth are exemplary communication protocols that can be used, and other communication protocols and specifications can be used in other embodiments of the body area network 101.

In one embodiment, the system 100 further comprises a medical server 109, which is communicatively coupled to the controller 102 via a network 108. The network 108 may be any type of network known in the art, including, for example, Ethernet, analog cellular, digital cellular, short range radio wireless, Wi-Fi, WiMax, broadband over power line, coaxial cable, and the like.

During operation, the controller 102 communicates with the plurality of sensors 103-106 to collect physical and/or physiological data related to the body 107 of the user 110. The data collected can be uneventful and historical in nature, and such data can be used to as a physical and/or physiological baseline for the user 110. In addition, the sensors 103-106 may also be triggered to perform specific data collection functions in response to an uncharacteristic event. Such data may be transmitted to the controller 102, and the controller 102 can, in turn, transmit the data collected in response to the event to the medical server 109.

In one embodiment, the medical server 109 may be monitored. Thus, in response to the uncharacteristic event, medical personnel may be alerted so that the user can obtain requisite medical attention. In another embodiment, the controller 102 relays information obtained from the sensors 103-106 to the medical server. In this regard, the medical server 109 may comprise a web portal (not shown), email and texting capabilities for interface with the user 110 and control of the system 100.

The wireless sensor network system 100 performs a variety of functions related to the acquisition and analysis of the data collected. These functions are described in more detail hereafter.

Figure 2:
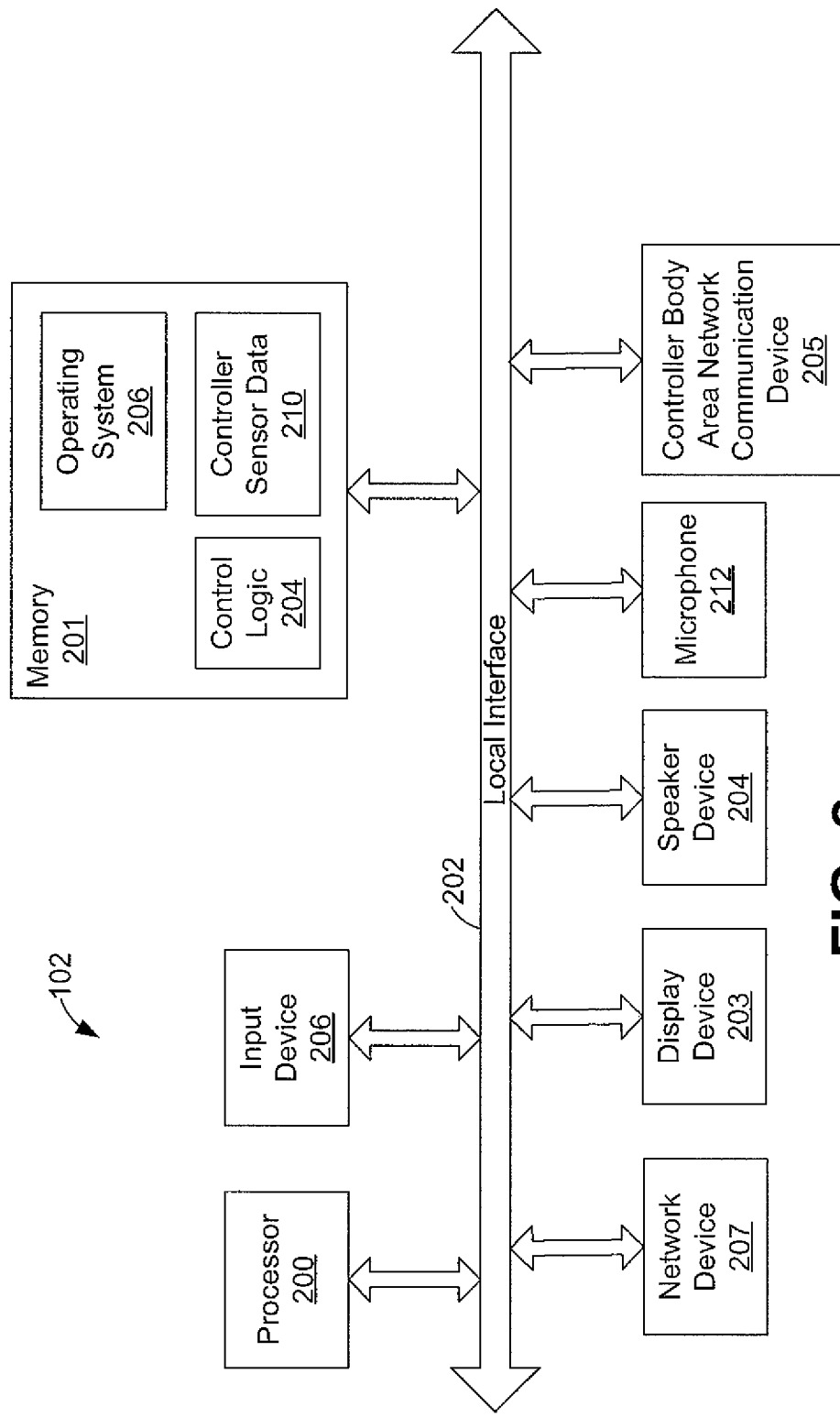
FIG. 2 is a block diagram of an exemplary controller of the wireless sensor network system depicted in FIG. 1.

FIG. 2 depicts an exemplary controller 102 of the present disclosure. The exemplary controller 102 generally comprises processor 200, display device 203, input device 206, network device 207, and controller body area network communication device 205. Each of these components communicates over local interface 202, which can include one or more buses.

Controller 102 further comprises control logic 204 and controller sensor data 210. Control logic 204 and sensor data 210 can be software, hardware, or a combination thereof. In the exemplary controller 102 shown in FIG. 2, control logic 204 and sensor data 210 are shown as software stored in memory 201. Memory 201 may be of any type of memory known in the art, including, but not limited to random access memory (RAM), read-only memory (ROM), flash memory, and the like.

As noted hereinabove, control logic 204 and sensor data 210 are shown in FIG. 2 as software stored in memory 201. When stored in memory 201, control logic 204 and sensor data 210 can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions.

In the context of the present disclosure, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium Processor 200 may be a digital processor or other type of circuitry configured to ran the control logic 204 by processing and executing the instructions of the control logic 204. By way of example, the processor 200 may be an Advanced RISC Machine ARM 7, ARM 9, Intel® PXA901, Intel 80386, Freescale® HCx08, Freescale® HCx11, Texas Instruments® MSP430, or a digital signal processor (DSP) architecture. Note that RISC refers to "Reduced Instruction Set Computer." The processor 200 communicates to and drives the other elements within the controller 102 via the local interface 202.

In addition, controller body area network communication device 205 may be, for example, a low-powered radio device, e.g., a radio semiconductor, radio frequency antenna (RF antenna) or other type of communication device, which communicatively couples the controller 102 with the sensors 103-106 (FIG. 1). The control logic 204 communicates bi-directionally through the controller body area network communication device 205 with the plurality of sensors 103-106.

The display device 203 is a device for visually communicating information to the user 110 (FIG. 1). The display device 203 may be, for example, a backlit liquid crystal display (LCD) screen (not shown), which is touch-sensitive for operation with a stylus (not shown). Other types of display devices may be used in other embodiments of the present disclosure.

An operating system 211, which may be, for example, Windows Mobile®, may display data, including commands, to the user 110 (FIG. 1) via a series of graphical user interfaces (GUIs) (not shown). The GUIs may comprise a plurality of scalable windows (not shown) that display, for example, data indicative of commands or analysis of information.

Controller sensor data 210 includes any data stored on the controller 102 related to the system 100 (FIG. 1), including data related to the sensors 103-106. Such sensor data 210 may include, for example, data indicative of particular readings or historical data of a plurality of readings received from one or more of the sensors 103-106 (FIG. 1). In addition, sensor data 210 may include configuration data specific to the user 110 that is using the controller 102.

Note that a "reading" refers to any data that is received from the sensors 103-106 that represents physical or physiological characteristics of the body 107 (FIG. 1) of the user 110. As described further herein, a reading may be requested from a sensor 103-106 by the controller 102 or a reading may be transmitted at a particular time interval pre-determined for the particular sensor 103-106 from which the controller 102 is requesting data.

The input device 206 enables the user 110 to enter data into the controller 102. In one embodiment, the input device 206 is a keyboard, and the user 110 uses the keyboard to type data into the handheld, which can be stored as sensor data 210, described hereinabove. In addition, the display device 203 may be a touch screen (not shown), and the controller 102 may comprise a stylus (now shown) that the user 110 can used to enter data via the touch screen (not shown).

In one embodiment, the controller 102 may comprise a speaker device 204 and a microphone 212. In such an embodiment, the controller 102 may audibly communicate commands and/or information to the user 110 via the speaker device 204. Furthermore, the user 110 may provide information to the controller 102 by speaking into the microphone 212.

During operation, the control logic 204 configures the system 100. In one embodiment, the user 110 may take some controller-directed action, e.g., placing sensors on the body 107, however, in other embodiments, the control logic 204 can autonomously discover the sensors 103-106 without action by the user 110.

In this regard, the control logic 204 initially discovers the sensors 103-106 that are proximate to the controller 102 for use in the body area network 101. To discover the sensors 103-106, the control logic 204 broadcasts a wireless discovery message. A "wireless discovery message" refers to a message that can be transmitted through the body area network 101 (FIG. 1) by the control logic 204 through the controller body area network communication device 205. This message is received by the sensors 103-106 and handled by each sensor 103-106 accordingly. Communication protocols, e.g., Zigbee® and Bluetooth®, define such a wireless discovery message. Notably, however, any type of communication protocol known in the art that includes a wireless discovery message may be used in other embodiments.

As an example, the wireless discovery message, by its particular format, may request all sensors 103-106 that receive the wireless discovery message to respond. In one embodiment each sensor 103-106 transmits, in response to the wireless discovery message, data indicative of its unique hardware address associated with the responding sensor 103-106. Thus, the control logic 204 can uniquely identify each discovered sensor.

Upon receipt of a response from each sensor 103-106, the control logic 204 stores as controller sensor data 210 data indicative of each responding sensor 103-106 and their corresponding hardware address. Once the discovery process is complete, the control logic 204 has identified sensors 103-106 by their corresponding hardware address and stored controller sensor data 210 reflecting the characteristics of each sensor 103-106.

Once the control logic 204 discovers the sensors 103-106 available to the system 100, the control logic 204 assigns to each sensor a logical function within the body area network 101. Given a homogeneous set of wireless sensors 103-106 with sufficiently similar capabilities, such that any two sensors 103-106 can be interchanged, the control logic 204 prompts the user 110 to place the sensors 103-106 on the body 107. In one embodiment, the control logic 204 may prompt the user 110 visually via a graphical user interface (GUI) displayed to the display device 203. In another embodiment, the control logic 204 may prompt the user 110 audibly via the speaker device 204. Other prompts may be used to instruct the user 110 to place the sensors 103-106 on the body 107 in other embodiments.

The control logic 204 prompts the user 110 in sequence to place a sensor 103-106 on the body 110 in a specified location. As an example, the control logic 204 may prompt the user with the following command: "Place a sensor on your chest." In one embodiment, each sensor 103-106 comprises an accelerometer (not shown) for motion sensing. Thus, the user 110 need not know the identity of the sensor the user 110 selects. Instead, the control logic 204 monitors the sensors 103-106 thereby autonomously requesting measures of movement, and control logic 204 detects which sensor 103-106 is experiencing the greatest movement based upon the measures received. In this regard, the user 110 is free to select a sensor 103-106 at random and place it in the location identified in the command. The control logic 204 then associates the hardware address with the location in the sensor data 210.

The control logic 204 then prompts the user 110 with another command: "Place a sensor on your right wrist." Again, the control logic 204 detects movement of the sensor 103-106 that is being placed, and records as sensor data 210 the hardware address associated with the moving sensor 103-106 with the location identified in the command. The control logic 204 continues this process until each of the sensors 103-106 discovered during the discovery process is placed on a location on the body 107 of the user 110.

In one embodiment, during assignment of sensors 103-106 with body locations, the control logic 204 dynamically reconfigures each sensor 103-106 to perform a function specific to the location on which the sensor 103-106 was placed. For example, the sensor 103-106 that is placed on the chest is dynamically reconfigured, for example, to monitor heart rate. As another example, the sensor 103-106 that is placed on the wrist is reconfigured, for example, to monitor oxygen saturation. In this regard, the control logic 204 transmits commands to the sensors 103-106 specifying particular algorithms to use. The control logic 204 also can transmit wireless firmware upgrades of each sensor 103-106.

In another embodiment, the control logic 204 completes the assignment process prior to reconfiguring the sensors 103-106. Once assignment of each sensor 103-106 to a particular location is complete, the control logic 204 reconfigures each sensor 103-106 to perform a function specific to the location on which the sensor 103-106 is placed.

In another embodiment, the control logic 204 also transmits information for dynamically reloading a microprocessor (not shown), which is part of the sensor 103-106. In this regard, the system 100 is resource-constrained, and it may be difficult for each sensor 103-106 to include each possible algorithm that might be needed based on an arbitrary location assignment as described hereinabove. In this case, the control logic 204 dynamically reloads the microprocessor instruction code to implement the desired function associated with the location arbitrarily selected by the user 110 for the particular sensor 103-106.

In another embodiment of the system 100, the sensors 103-106 may incorporate temperature sensors (not shown). The control logic 204 may obtain data from the sensors 103-106 indicative of the temperature increase realized by placing the sensor 103-106 on the body 107. The control logic 204 may use the temperature increase to determine which sensor 103-106 has been placed on a particular location on the body 107.

In another embodiment of the system 100, the sensors 103-106 use integrated electrodes for radiating the human body. When in contact with the skin, a small charge will generate a small current through the human skin, thus effectively measuring skin or body impedance. This current is detectable by the sensor 103-106, and the control logic 204 can determine that the sensor 103-106 is now in contact with human skin.

In another embodiment of the system 100, sensor discovery and assignment are an integrated function. This is especially useful if the sensors 103-106 are allowed to enter a low power state when not in use. In this case, the sensors 103-106 will originate communications with the control logic 204 of the controller 102 once they recognize an in-use event such as being placed on the body 107. An in-use event can be detected by the control logic 204 by listening for messages received from the sensors 103-106 and interpreting those messages received.

In addition to performing discovery and configuration of the system 100, the control logic 204 further performs calibration of the system 100. As described hereinabove, one or more of the sensors 103-106 may be used to determine a user's orientation or position through accelerometers. For example, data obtained from accelerometers on one or more sensors 103-106 may be used to indicate whether the user 110 is in a supine position or standing in an upright position.

Thus, in one embodiment of the present disclosure, the control logic 204 self-calibrates the system 100 to compensate for any offset caused by the placement of the sensors 103-106 on the user's body. Notably, it is the orientation of the user 110 wearing the sensors 103-106 in the system 100 that is relevant for determining movement of the user 110. However, placement of the sensors 103-106, because placement is arbitrary, may tend to effect readings made with respect to movement by skewing orientation of the actual user 110. Therefore, the control logic 204 calculates and calibrates a relative orientation.

Figure 3:
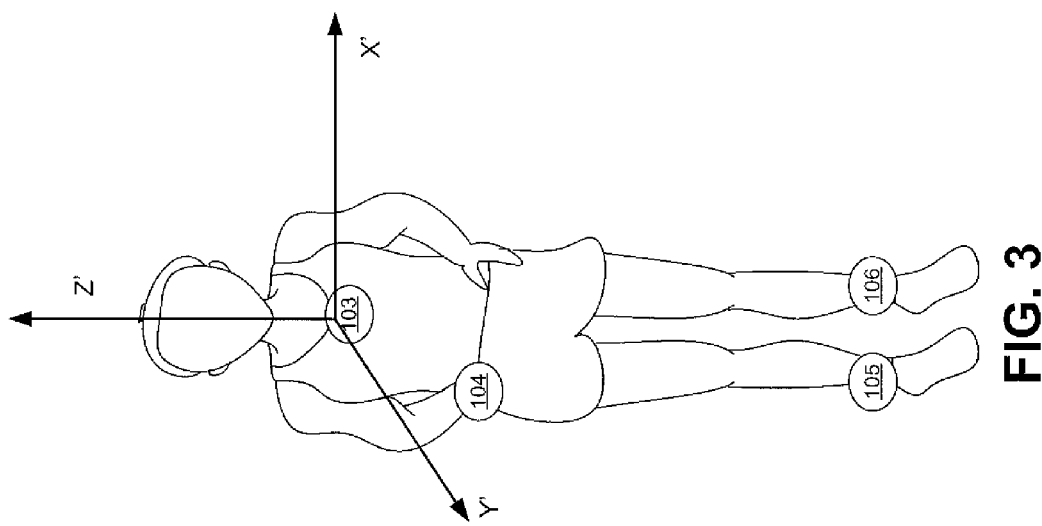
FIG. 3 is a drawing of a user's axes as used by a calibration function of the system depicted in FIG. 1.

As described hereinabove, the control logic 204 performs calibration to ensure that sensor readings for detecting movement are accurate in light of the placement of sensors 103-106 on the body 107 of the user 110. Calibration is now described in more detail with reference to FIGS. 3-7. To perform calibration, the control logic 204 instructs the user 110 to stand in an upright position, communicating with the user 110 as described hereinabove. When the user 110 is requested to stand in an upright position, the control logic 204 assumes that the user's body 107 is oriented along the X', Y' and Z' axes as shown in FIG. 3.

Figure 4:
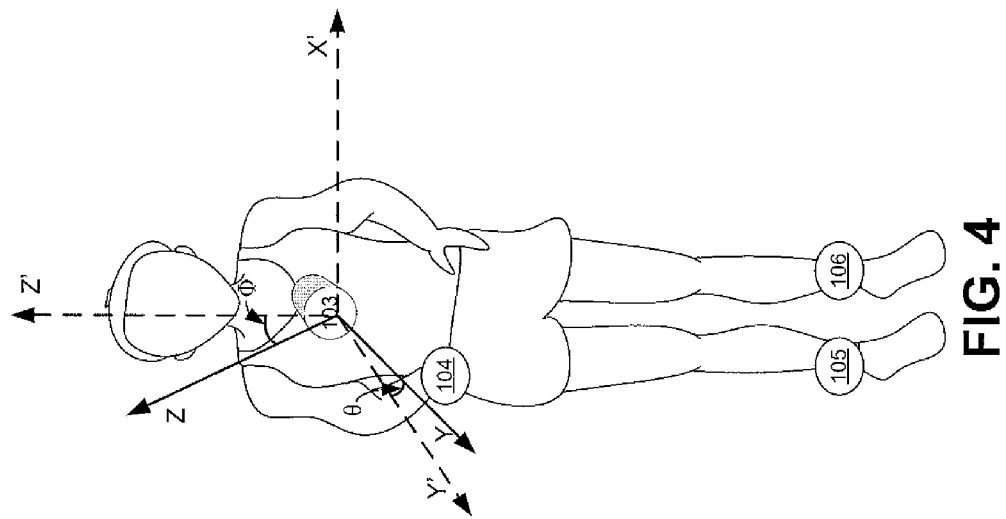
FIG. 4 is a drawing of a user's axes and a sensor's axes as used by a calibration function of the system depicted in FIG. 1.

The control logic 204 then determines the actual orientation of the sensors 103-106 and calculates a calibrating correction factor. With reference to FIG. 4, the sensor 103 is shown as placed upon the chest area of the body 107. The sensor 103 is shown as rotated forward about the Y axis creating two angle offsets: θ (angle between the sensor's X axis and the user's X' axis) and Φ (angle between the sensor's Z axis and the user's Z' axis). The control logic 204 calculates the calibration angles θ and Φ by applying a theorem that the static effects of gravity will only affect the Z' axis in a magnitude of 1 g.

Figure 6:
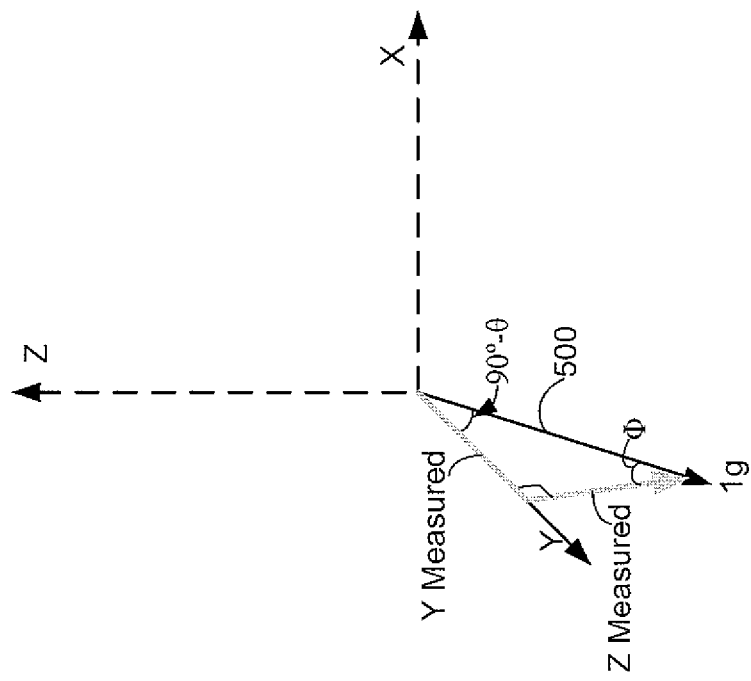
FIG. 6 is a drawing of a sensor's axes and a gravity vector as used by a calibration function of the system depicted in FIG. 1.
Figure 5:
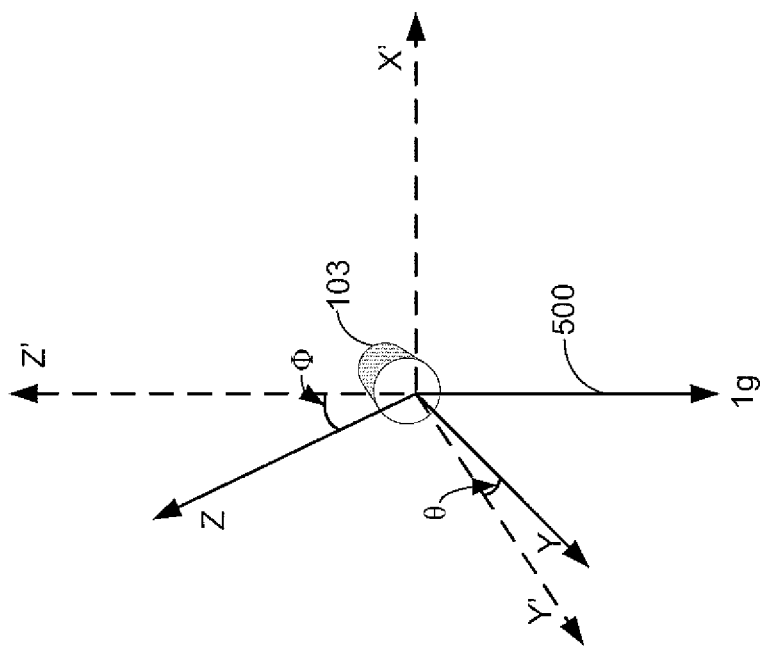
FIG. 5 is a drawing of a user's axes and a sensor's axes including the effect on the Z' axis of gravity as used by a calibration function of the system depicted in FIG. 1.

Thus, with reference to FIG. 5, gravity vector 500 represents the effect of gravity relative to the sensor's axis system (X',Y', and Z'). Further, FIG. 6 depicts the gravity vector 600 as it relates to the sensor 103. Therefore, the control logic 204 can calculate the angles θ and Φ by receiving measurements from the sensor 103 in the X direction and the Z direction and calculating as follows:

$$\theta = \sin^{-1}\left(\frac{x_{measured}}{1g}\right)$$

$$\phi = \cos^{-1}\left(\frac{z_{measured}}{1g}\right)$$

Once the angles θ and Φ are calculated, the control logic 204 can use the calculated offset angles θ and Φ to determine the orientation of the body 107 of the user 110 as the body 107 moves. In this regard, as the body 107 moves, the control logic 204 obtains new measurements from one or more sensors 103-106, and the control logic 204 uses the offset angles θ and Φ to calculate the orientation of the body 107 as it moves.

Thus, as an example, with reference to FIG. 7, the user 110 moves his body 107 and creates an angle, γ, between the original calibrated Z' axis and true vertical Z" axis. The control logic 204 can calculate γ from the sensor measurements as follows:

$$\gamma = \cos^{-1}\left(\frac{z_{measured}}{1g}\right) - \phi$$

Note that any of the axes X', Y', and Z' may have associated with it an initial offset depending upon the location of the sensor 103-106 (FIG. 1). Only an offset θ and Φ in relation to the X' and Z', respectively, are shown calculated in the example provided hereinabove. However, in addition, there may also be an offset Ω corresponding to the Y' axis. Furthermore, FIG. 7 illustrates a calculation of only an angle γ for the Z' axis, however angles α and β may be calculated for angles corresponding to X' and Y', respectively.

Notably, given three initial offsets θ, Ω, and Φ with respect to the X', Y', and Z' axes respectively, the user's angles of orientation α, β, and γ with respect to X', Y', and Z' respectively can be calculated as follows:

$$\alpha = \sin^{-1}\left(\frac{x_{measured}}{1g}\right) - \theta$$

$$\beta = \sin^{-1}\left(\frac{y_{measured}}{1g}\right) - \Omega$$

$$\lambda = \cos^{-1}\left(\frac{z_{measured}}{1g}\right) - \phi$$

This method is directly applicable to cases where sensor nodes are placed upside down (180 degree rotation). This method is also extensible to other zero-state configurations (other than standing) such as sitting, lying, or combination of multiple initial state calibrations.

Furthermore, the sensor 103-106 for detecting motion may also be subject to a wide range of factors, which could degrade performance. Notably, temperature, humidity, and power supply voltage can affect sensor performance. When affected by such factors, the control logic 204 may determine the actual affect of the relevant factor, e.g., temperature, and define a transfer function for describing the sensor readings when the sensor 103-106 is affected. When defining a transfer function is possible, other sensors (not shown) can be used to collect information for the transfer function so that the control logic 204 can compensate for the affects as these factors may vary over time and change after the initial calibration.

As an example, an ambient air temperature sensor (not shown) could be used to obtain varying temperature readings. The control logic 204 can use these varying temperature readings with the transfer function defined in order to compensate for the affects of the varying temperature. In addition, the same method could be used with a humidity sensor to compensate for degradation of the motion sensor 103-105 as a function of humidity, and a voltage measuring sensor to compensate for degradation of the motion sensor as a function of supply voltage.

Figure 8:
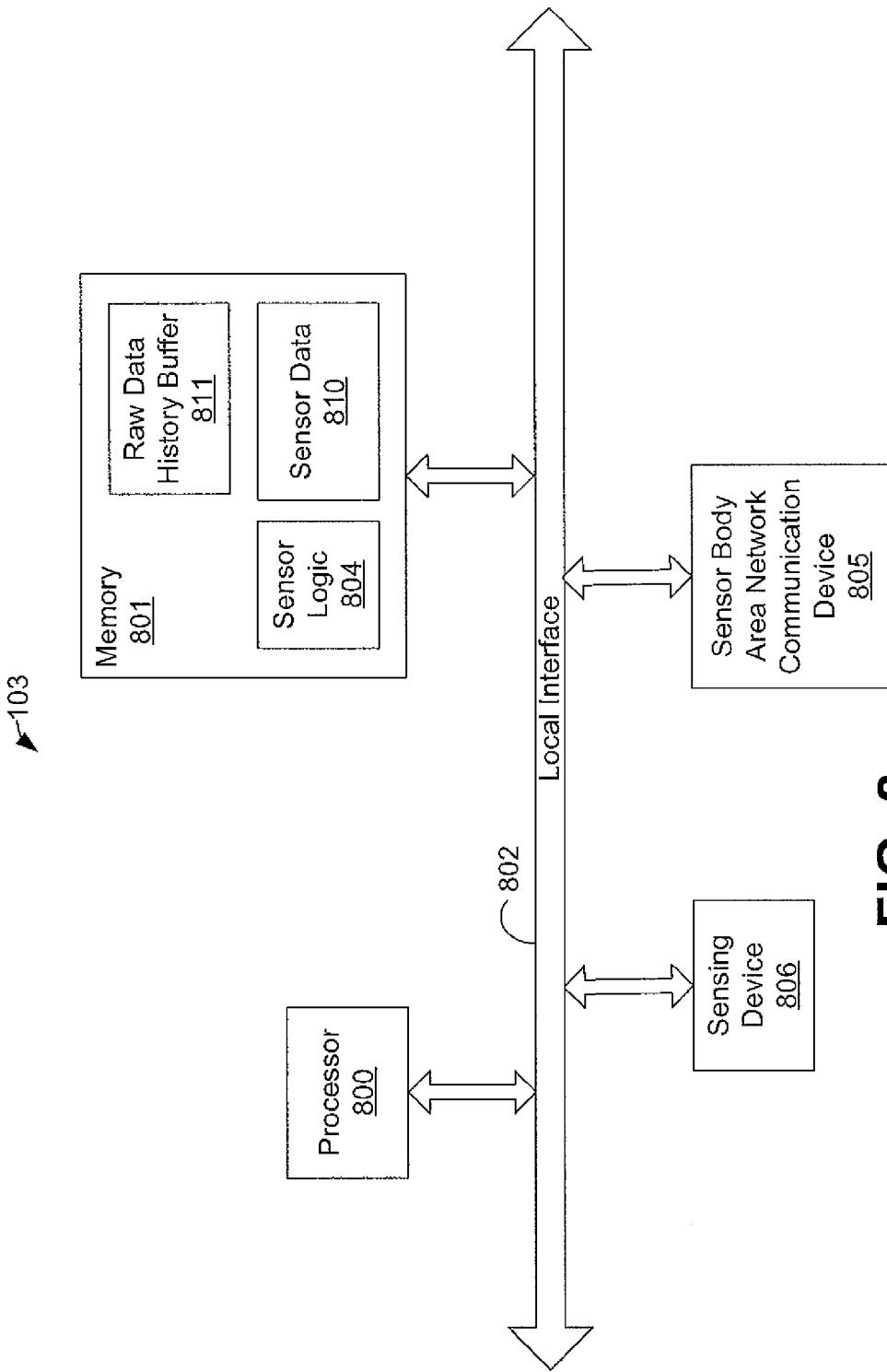
FIG. 8 is a block diagram of an exemplary sensor of the wireless sensor network system depicted in FIG. 1.

FIG. 8 depicts an exemplary sensor 103 of the present disclosure. As indicated hereinabove, in one embodiment the sensors 103-106 are substantially similar. In this regard, the sensors 103-106 may be characteristically homogeneous, however if they differ, they could differ in the type of sensing hardware employed and/or the software employed to collect the data. For purposes of brevity, only sensor 103 is discussed hereinafter. However, the other sensors 103-106 behave substantially similar.

The exemplary sensor 103 generally comprises processor 800, a sensing device 806, and sensor body area network communication device 805. Each of these components communicates over local interface 802, which can include one or more buses.

Sensor 103 further comprises sensor logic 804 and sensor data 810. Sensor logic 804 and sensor data 810 can be software, hardware, or a combination thereof. In the exemplary sensor 103 shown in FIG. 8, sensor logic 804 and sensor data 810 are shown as software stored in memory 801. Memory 801 may be of any type of memory known in the art, including, but not limited to random access memory (RAM), read-only memory (ROM), flash memory, and the like.

As noted hereinabove, sensor logic 804 and sensor data 810 are shown in FIG. 8 as software stored in memory 801. When stored in memory 801, sensor logic 804 and sensor data 810 can be stored and transported on any computer-readable medium for use by or in connection with an instruction execution system, apparatus, or device, such as a computer-based system, processor-containing system, or other system that can fetch the instructions from the instruction execution system, apparatus, or device and execute the instructions.

In the context of the present disclosure, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

Processor 800 may be a digital processor or other type of circuitry configured to run the sensor logic 804 by processing and executing the instructions of the sensor logic 804. By way of example, the processor 800 may be an Advanced RISC Machine (ARM) 7, ARM 9, Intel® PXA901, Intel 80386, Freescale HCx08, Freescale® HCx11, Texas Instruments® MSP430, or a digital signal processor (DSP) architecture. Note that RISC refers to "Reduced Instruction Set Computer." The processor 800 communicates to and drives the other elements within the sensor 103 via the local interface 802.

In addition, sensor body area network communication device 805 may be, for example, a low-powered radio device, e.g., a radio semiconductor, radio frequency antenna (RF antenna) or other type of communication device, that communicatively couples the sensor 103 with the controller 102 (FIG. 1). The sensor logic 804 communicates bi-directionally through the sensor body area network communication device 805 with the controller 102.

The sensing device 806 may be, for example, heart waveforms sensors, respiration sensors, and muscle activity sensors, SpO₂ sensors, and/or GSR sensors. Further, the sensing device 806 may be an electrode for detecting current from the skin (not shown) of the body 107. These are exemplary types of sensing devices, however, other types of sensing devices may be used in other embodiments of the present disclosure.

Sensor data 810 refers to data related to the sensing device 806. In this regard, the sensor data 810 may be, for example, data indicative of readings received from the sensing device 806. In addition, sensor data 810 may encompass configuration data specific to the user 110 (FIG. 1) that is using the controller 102 (FIG. 1) and the sensor 103.

In one embodiment, the controller 102 (FIG. 1) and the sensor 103 work in conjunction to perform event management and contextual event data delivery. Event management refers to the receipt, storage, and identification of data indicative of an event. An "event" refers to an occurrence evidenced by a change in data detected by the sensing device 806.

In one embodiment, in order to accomplish event management, the sensor logic 804 assesses a timestamp for each reading obtained by sampling a signal received by the sensing device 806. The data that receives the timestamp is not immediately transmitted to the controller 102 (FIG. 1). Instead, the sensor logic 804 defers transmission of the data until the particular sensor's assigned transmission interval. Such timestamped data indicative of the reading is stored as sensor data 810, and such timestamp is associated with the reading prior to any on-sensor operations performed on the reading to determine whether an event has occurred.

In addition, the sensor logic 804 performs contextual data delivery. "Contextual data delivery" refers to the transmission of data related to an event, as described hereinabove, to the controller 102.

In one embodiment in order to perform contextual data delivery, the sensor logic 804 stores raw data in a raw data history buffer 811. Further, the sensor logic 804 performs operations on the data stored in the raw data history buffer 811 to determine if an event has occurred. As an example, a sensing device 806 may be configured to detect an analog heart rate signal, and the sensing device 806 samples the signal periodically to obtain a reading. Once a reading is obtained, the sensor logic 804 stores the raw data indicative of the reading in the buffer 811. The sensor logic 804 may analyze a plurality of readings over a pre-determined time period, for example five minutes. If there is a sharp increase in the value of the reading, this may indicate an event. Thus, the sensor logic 804, after its analysis to determine that an event may have occurred, may transmit the raw data in the buffer 811 to the controller 102.

In another embodiment, the sensor logic 804 transmits readings and associated timestamps to the controller 102. The controller 102 detects an event and transmits a message to the sensor 103 to enable raw data mode thereby allowing the sensing logic 806 to continually transmit raw data from the history buffer 811 to the controller 102 until the pertinent event has expired.

Figure 9:
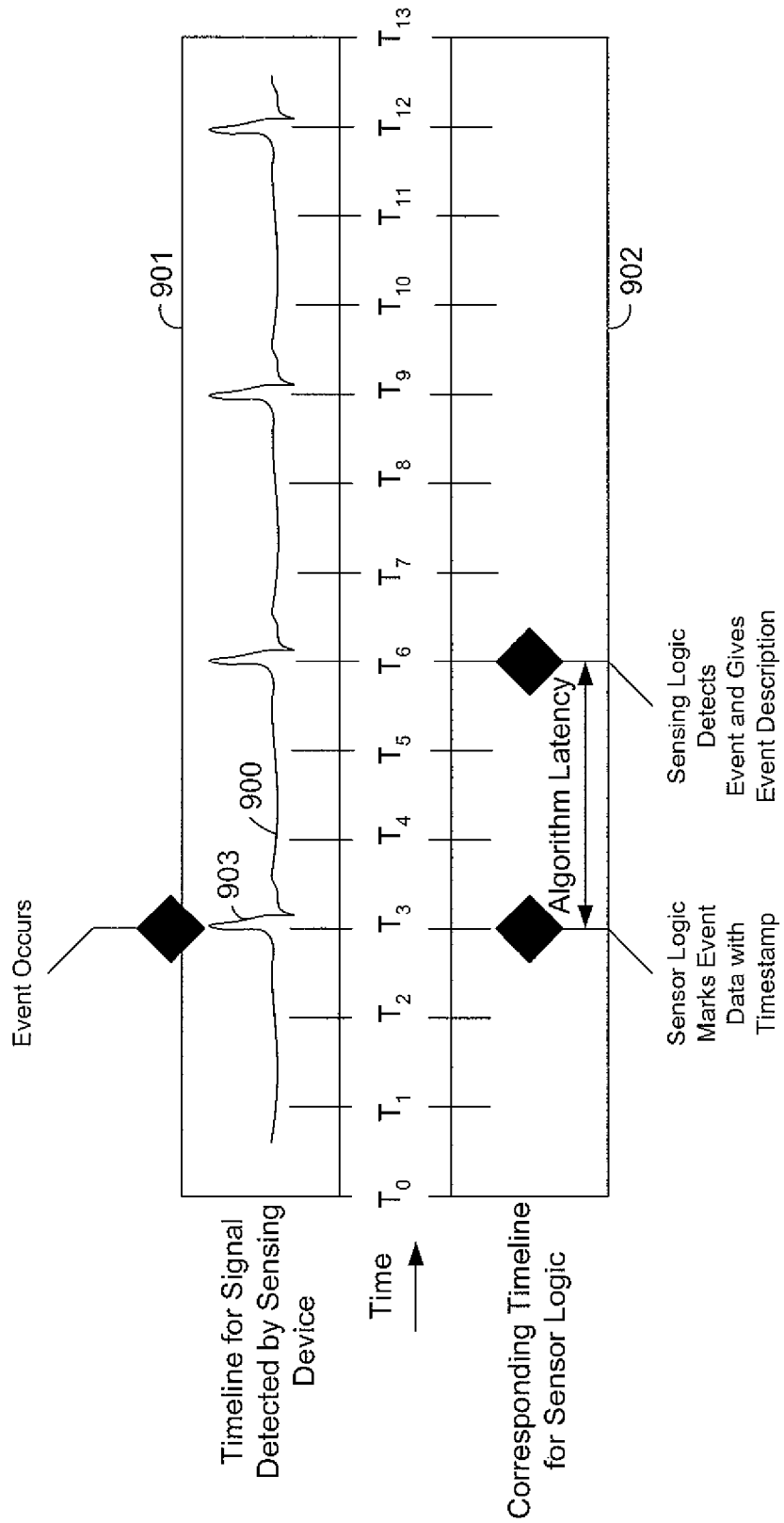
FIG. 9 is a timeline depicting an algorithm latency illustrating event management as performed by the system of FIG. 1.

To further illustrate event management performed by the sensor 103 and the controller 102, FIG. 9 depicts a timeline 901 and a corresponding timeline 902. Timeline 901 depicts a signal 900 received by the sensing device 806 (FIG. 8) over time, $T_0$ to $T_{13}$. Timeline 902 depicts functionality of the sensor logic 804 over time, $T_0$ to $T_{13}$.

In the illustration, the sensor 103 detects a change in the monitored signal 900 (event) such as environmental data, physiological data, or machine health data. Such a change is evidenced by a spike 903 in the monitored signal 900. Based on a network time reference, the sensor logic 804 assesses an "original timestamp" to the event occurrence at $T_3$ when the spike 903 occurs. The original timestamp is prior to any on-sensor processing time, independent of latency in utilizing any on-sensor resource (memory or other), and independent of network transmission time which can vary widely depending on the organization of the network and the variability inherent in heterogeneous networks. Notably, at time $T_6$ the sensor logic 804 detects the event and gives the event description. However, algorithm latency has occurred prior to the detection and description.

When the event detection algorithms require some finite execution time, as illustrated, the timestamp provided by the sensor logic 804 is independent of algorithm latency. Thus, in one embodiment, the sensor logic 804 assesses timestamps to each data point of sampled signal 900. When the sensor logic 804 determines the occurrence of an event, the earlier data point timestamp (assessed on the original data point) can be used as the timestamp for the occurrence of the event.

Figure 10:
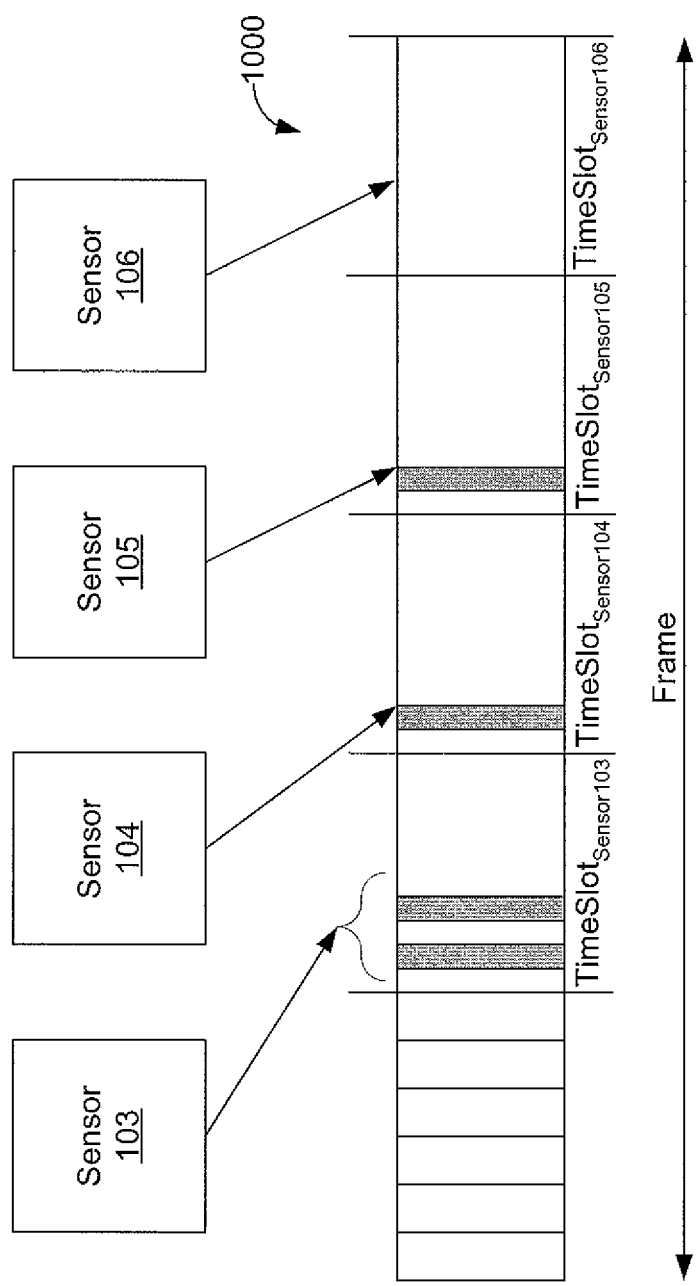
FIG. 10 is a block diagram of a data frame as used by the system of FIG. 1.

In one embodiment, the control logic 204 (FIG. 2) of the controller 102 (FIG. 1) assigns specific time intervals for each sensor's respective transmission or receptions. FIG. 10 depicts a block diagram of a communication frame 1000 in accordance with such an embodiment.

The exemplary communication frame 1000 assumes the sensors 103-106 (FIG. 1) are all-inclusive of those sensors in the body area network 101 (FIG. 1) for the example. Each sensor 103-106 collects data related to the signals that each sensor monitors. In one embodiment, the control logic 204 (FIG. 2) defines the frame 1000 to encompass a node command block, which can include binary digits reflecting a command to one or more of the sensors 103-106. In addition, the control logic 204 defines a block of time slots TimeSlot$_{sensor103}$-TimeSlot$_{sensor106}$. Notably, the control logic 204 would define a timeslot for transmission and reception for each sensor 103-106 in the node. In the example used throughout the present disclosure, four sensors 103-106 are shown in the body area network 101. Thus, for continuity, four sensors 103-106 are used in the example provided in FIG. 10.

In such an embodiment, the control logic 204 assigns a TimeSlot$_{sensor103}$ to the sensor 103, which may be a heart beat sensor. In addition, the control logic 204 assigns TimeSlot$_{sensor104}$ to the sensor 104, which may be a motion sensor.

Thus, an event occurs, for example a heart beat event occurs, which is detected by sensor 103, and a step event occurs, which is detected by sensor 104. The sensors 103 and 104 do not immediately transmit data to the controller 102 indicative of the heartbeat and step events. Instead, the sensors 103 and 104 wait until their respective time slots occur, and transmit the data during their respective time slots.

As described hereinabove, the event descriptions can be time stamped by the sensor logic 306 as they occur so as to not incur latency and jitter from deferred transmission artifacts. This allows faithful reproduction of the original events with proper timestamps independent of the actual transmission time.

Such an embodiment may require a synchronized network time reference, as described hereinabove. Thus, each sensor 103-106 and the controller 102 operate from a synchronized clock cycle. Thus, each sensor 103-106 knows when its corresponding time slot is ready for transmission and/or reception. In such an embodiment, a synchronization protocol, e.g., the Flooding Time Synchronization Protocol (FTSP), can be used to distribute a common time reference.

In another embodiment of the wireless sensor network system 100, reliability of the network transmission is not guaranteed. Sensors 103-106 can lose power, intermediate nodes (not shown) in multi-hop networks may exit without warning, in mobile networks the network topology can change without warning or leave range entirely, or outside factors may impair the ability of the wireless media to perform as expected. These conditions can be detected so that the sensor logic 804 can maintain the state of the network 101. Reliability and performance are improved when the sensors 103-106 perform autonomous detection of network changes.

In one embodiment, the controller 102 transmits periodic beacon messages. The sensor logic 804 receives the beacon messages from the controller 102 via the sensor body area communication device 805, and infers successful connectivity with the controller 102 by receipt of the periodic beacon message. When the beacon message arrives in a timely fashion, the sensor logic 804 can assume the network is operable;

conversely when an allowable time period expires without beacon arrival, the sensor logic 804 can assume that the network is inoperable.

In another embodiment, the control logic 204 transmits an explicit acknowledgement message to verify that a message transmitted from the sensor 103-106 has been received by the controller 102 (FIG. 1). Thus, if the message is lost by an intermediate node (not shown) in the network 101 where the network 101 supports one hop or multi-hop transmission, the sensor logic 804 does not receive the acknowledgement message. In such a scenario, the sensor logic 804 employs a timeout mechanism that determines that the acknowledgement message did not arrive and behaves accordingly. Note that it is possible for one or more messages to be en route at any given time and the messages (or events) must be preserved as sensor data 810 (FIG. 8) on the sensor 103-106 and cannot be retired until the message or messages are acknowledged.

Figure 11:
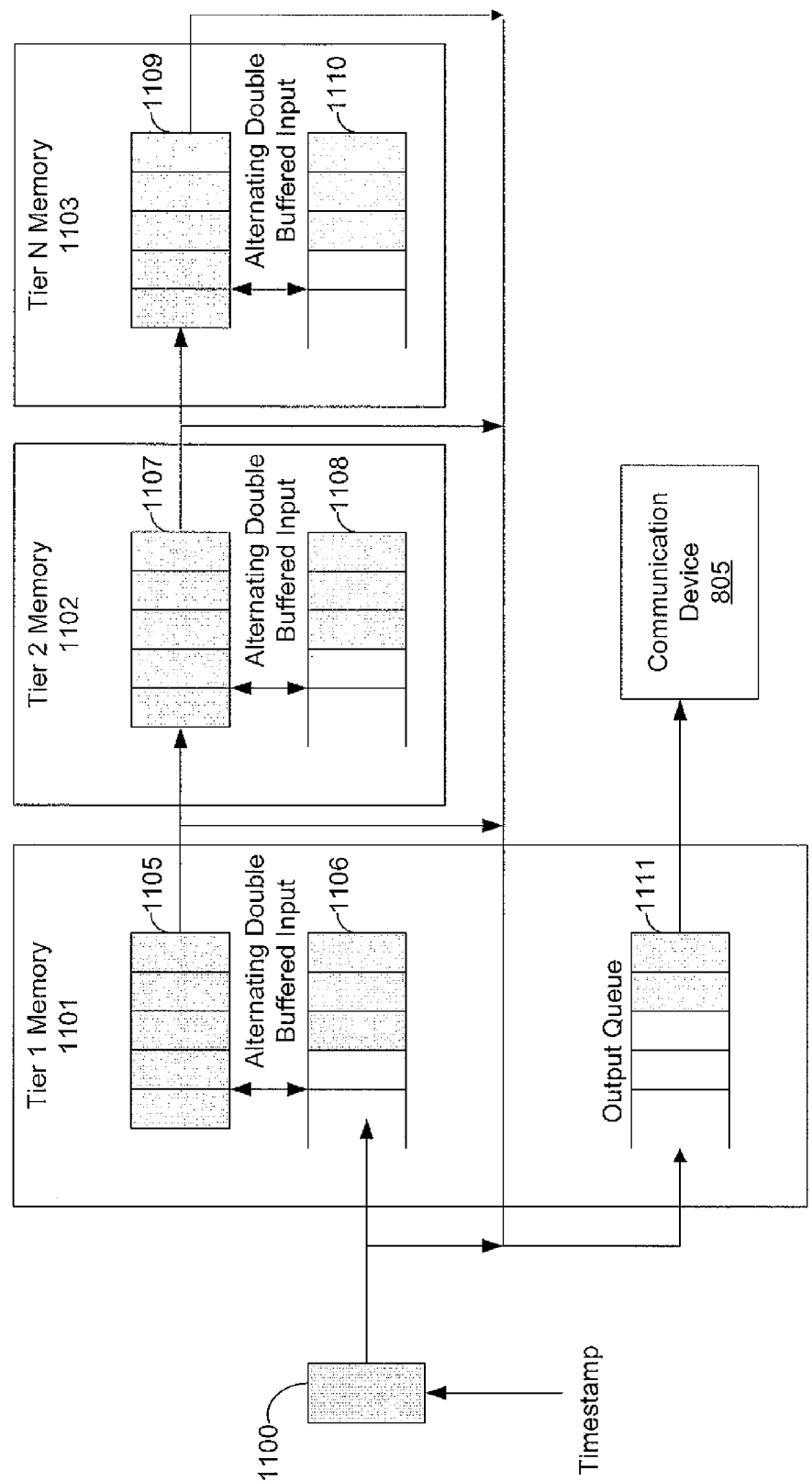
FIG. 11 is a block diagram of multi-tiered memory architecture as used by the system of FIG. 1.

FIG. 11 depicts a memory hierarchy for a sensor 103-106 (FIG. 1) and illustrates another embodiment of an event management method. In one embodiment of the system 100 (FIG. 1), the sensor logic 804 (FIG. 8) minimizes latency by transmitting event data when the event occurs. Based on autonomous detection of network changes, as described hereinabove, data indicative of events are stored in memory 801 (FIG. 8) for immediate transmission or for buffering to raw data history buffer 811 (FIG. 8).

In memory constrained systems, the available memory may have varying costs in terms of power and time latency such that the memory devices can be arranged hierarchically in order of preference. Moreover, events should first be buffered in the lowest penalty memory device, and, only on exhaustion of this resource, begin buffering in the next lowest penalty memory device, and so on. As an example, the sensor logic 804 can store the data in memory 801 hierarchically from lowest penalty to highest penalty, for example as follows: on-chip RAM, off-chip RAM, on-chip flash, off-chip flash. One embodiment places value on minimizing latency in delivering messages to the controller 102. The sensors 103-106 may be memory-constrained and comprise multi-tiered memory components, including an output queue 1111, "Tier 1 Memory" 1101, "Tier 2 Memory" 1102 through "Tier N Memory" 1103.

It is recognized that in real-time applications the memory devices 1101, 1102, and 1103 may incur time penalties for storage and retrieval. As a non-limiting example, flash memory may be employed with erase and program times measured in tens or even hundreds of milliseconds. When the application cannot tolerate this latency, a method for overlapping the operations is employed so that lowest penalty memory device is always available for event buffering. This is accomplished by using a double buffered approach at each tier in the memory hierarchy. Thus, at each tier 1101-1103 double buffers 1105/1106, 1107/1108, and 1190/1110 are maintained.

During operation, when a threshold number of events is reached, a block of events are moved, i.e., copied, to next tier storage while still maintaining a separate first-tier resource buffer for subsequent events that occur prior to completion of the move. The depth of the buffers 1105 and 1107 is selected to accommodate the maximum rate of event occurrence given the worst-case latency on the memory device. In one embodiment, the size of the buffers 1105 and 1107 is chosen for efficiency and optimized to be a multiple of the natural block size of the next-tier memory device.

In one embodiment, when the sensor logic 804 autonomously detects the availability of the network 101 (FIG. 1), the sensor logic 806 will trigger retiring buffered events in a first in, first out (FIFO) fashion. Where retrieving event from higher tier memory devices has a large penalty, the buffered event blocks can first be copied into the lowest penalty memory device forming the output queue 1111. In such an embodiment, once one event is successfully transmitted by the sensor body area communication device 805, the event data can be moved from a higher tier device, e.g., Tier N Memory 1103, and transmitted from the sensor 103 (FIG. 8) so that the event data can be permanently retired.

Thus, the sensor logic 804 defines and timestamps an event 1100. It is stored in the buffer 1106, and as new events are received from the sensor logic 804, the event 1100 is moved, i.e., copied to the second buffer 1105. As the resources are used up in Tier 1 Memory 1101, the event 1100 is moved to Tier 2 Memory 1107, and so on. When the sensor logic 804 decides to transfer data related to a particular event, the data is moved to the output queue 1111, and then to the sensor body area communication device 805.

Likewise, autonomous detection of the network's availability will trigger the oldest events to begin transmission and to begin effectively retiring these buffered events in a first in, first out (FIFO) fashion. In cases where retrieving events from higher tier memory devices has a large penalty, it is recognized that buffered event blocks can be first be copied into the lowest penalty memory device forming an output queue. Successful transmission of one block will trigger the fetch of the next oldest block and so on so that old events are systematically moved from higher tier devices and transmitted off-sensor so that they can be permanently retired.

Once the body area network 101 is operational for a period of time, all the event data in the higher tiers have been retired, events data can be queued directly to the output queue 1111 to maintain real-time transmission capability. If the network becomes inoperable again, event data can then be stored again in the tiered fashion described hereinabove.

In addition to event management, the system 100 performs contextual event data delivery. "Contextual event data delivery" refers to the function of recognizing and extracting data indicative of pertinent events in order to maximize scalability of the system 100 and minimize power consumption on the sensor 103-106.

Notably, power consumption and other resources in the system 100 can be conserved by performing in-system real-time signal processing to extract features and events directly on the sensor node and avoiding expensive multiple transmissions for post data reduction. Also, the more data available, the better a signal can be faithfully reproduced. In many cases a sensor 103-106 monitors a given signal or parameter for extended periods of time only looking for a specific event occurrence which may happen infrequently. In such cases, it would be inefficient to transmit all raw data indicative of the event as the end user (not shown) may only be interested in inspection of a small window of time surrounding the event.

In one embodiment, the sensors 103-106 in the wireless network 101 perform a substantial level of on-sensor processing extracting only data indicative of particular events. Upon detection of an event by the sensor 103-106, the sensor 103-106 autonomously transitions to raw data mode so as to provide maximum context for the event of interest. After some period of time the sensor 103-106 autonomously returns to reduced data (event only) mode.

In one embodiment, the sensor 103-106 includes a circular history buffer (not shown) which continuously stores raw event data for some finite period of time. In such an embodiment, when the sensor logic 804 detects an event, the sensor 103-106 transmits the circular history buffer, which represents context prior to the event of occurrence. In addition, the sensor logic 804 transmits raw event data following the event of interest. The amount of data transmitted after the event may vary. In this regard, it may be an amount defined by the number of bits to be transmitted or defined by a time period of collection.

Figure 12:
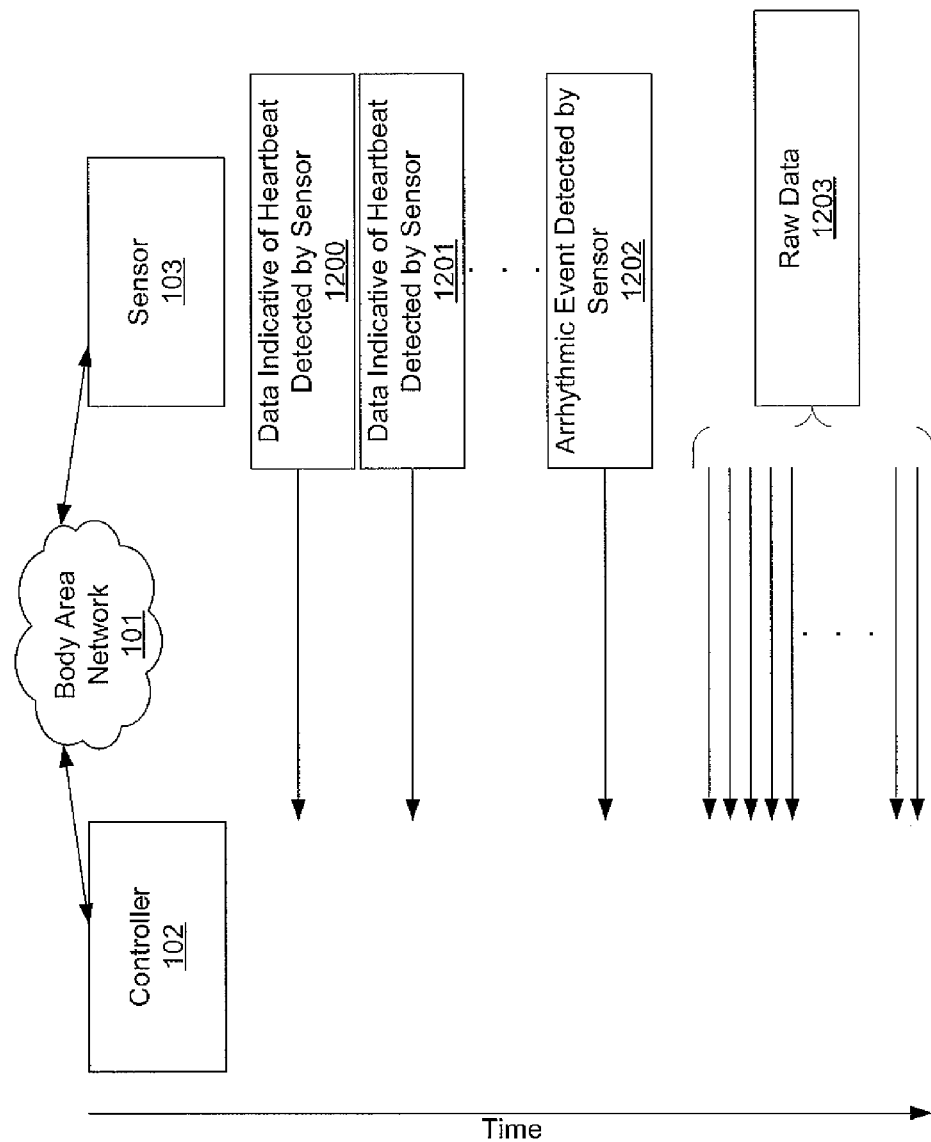
FIG. 12 is a timeline illustrating the contextual data delivery functionality of the system of FIG. 1.

FIG. 12 depicts one embodiment of the functionality of system 100 related to contextual event data delivery. As has been described throughout, controller 102 communicates with the sensor 103 via the body area network 101. In the example in FIG. 12, the sensor 103 is employed in a health monitoring application wherein the sensor 103 continuously monitors heartbeats in an attempt to look for arrhythmic events, heart-beat irregularities, or some other pertinent event. A treating physician may prefer to examine the raw heart waveforms immediately prior to and immediately following the arrhythmic event. The sensing device 806 (FIG. 8) receives regular heartbeats and the sensor logic 804 (FIG. 8) transfers data indicative of the heartbeats 1200, 1201, and so on, to the controller 102. In one embodiment, the data indicative of the heartbeats 1200, 1201, and so on, can be sent, via the network 108 (FIG. 1) to the medical server 109 (FIG. 1) where a physician or caregiver may inspect further.

When the sensing device 806 detects an arrhythmic event, the sensor logic 804 transmits data indicative of the arrhythmic event 1202 to the controller 102. The sensor logic 804 then transmits raw data 1203 continuously to the controller 102 so that the user can review the actual raw data that is being obtained by the sensing device 806.

Figure 13:
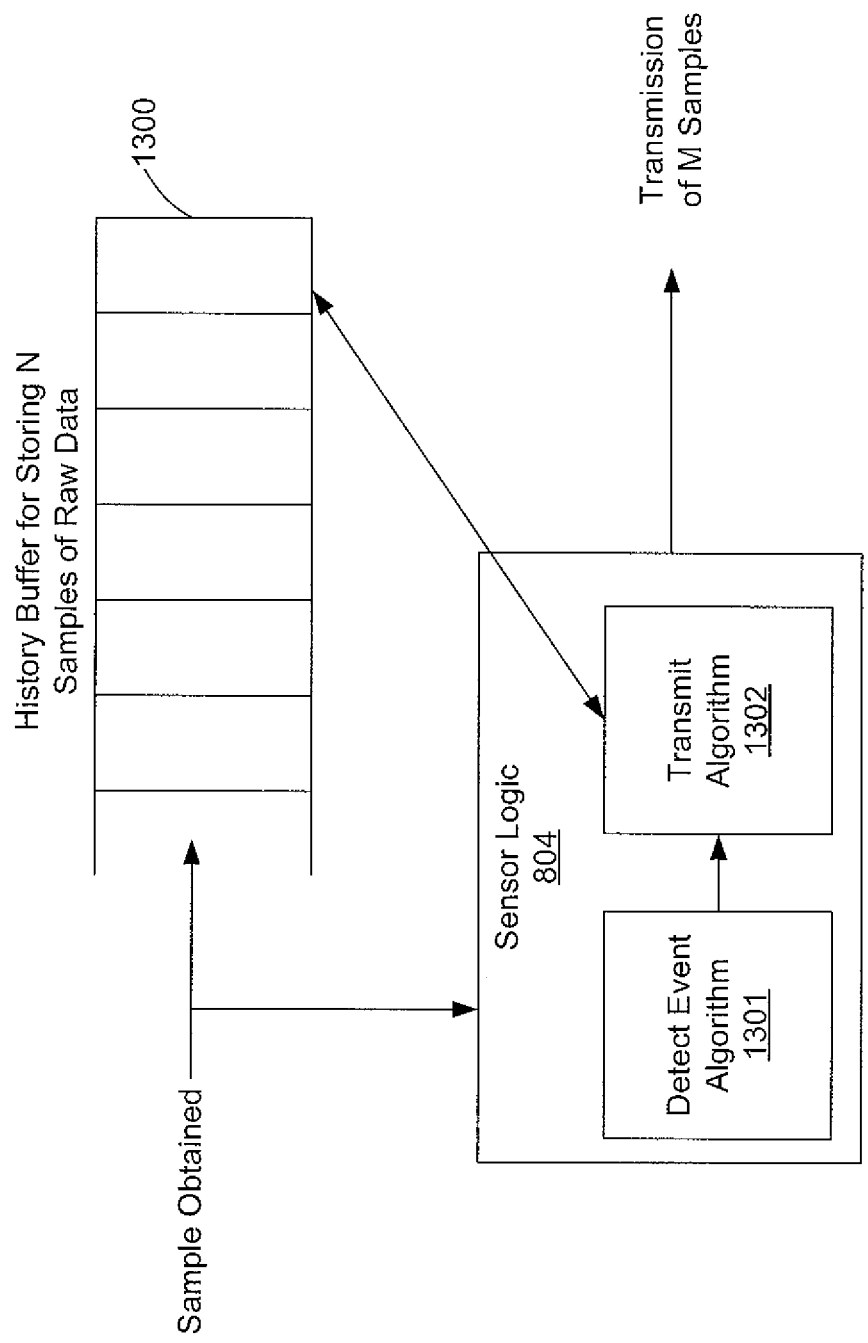
FIG. 13 is a block diagram illustrating the contextual data delivery function of the system of FIG. 1.

FIG. 13 is a block diagram depicting an exemplary software architecture and functionality for implementing the example depicted in FIG. 12. The sensor logic 804 receives raw data in response to an interrupt service routine (ISR). The sensor logic 804 stores the data in a history buffer 1300. Exemplary history buffers include a ring buffer (not shown) or a first in first out (FIFO) queue (not shown) with an overflow policy that retires old samples rather than new samples.

The history buffer 1300 stores the previous N samples of raw data where N represents the maximum number of samples of raw data that can be stored in the buffer 1300. The raw data samples are also provided as input to application-specific sensor logic 804, and the sensor logic 804 employs event detection algorithms 1301 for detecting a pre-defined event, for example an arrhythmic occurrence if the sensor logic 804 is designed to process heartbeat signals. In addition, the sensor logic 804 employs a transmit algorithm 1302 for retrieving event data from the history buffer 1300 and transmitting it to the controller 102.

Upon detection of an event by the event detection algorithm 1301, the transmit algorithm is signaled to begin transmission of M raw samples. M can be set by the needs of the application, but typically M=2N, so that upon event detection N preceding samples, where N is the depth of the existing history buffer prior to event detection, and the next N following samples will be transmitted thus providing balanced context of the specific event.

Figure 14:
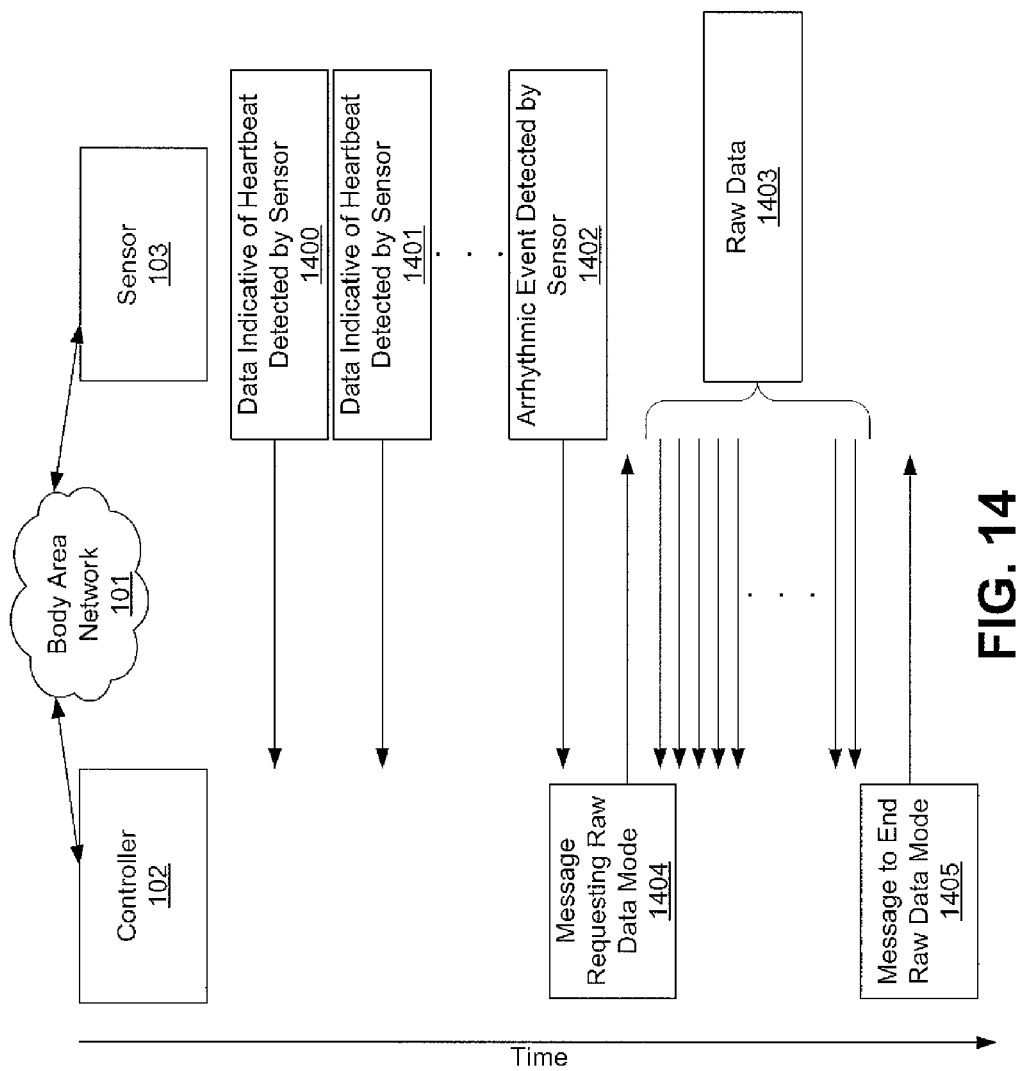
FIG. 14 is a timeline illustrating the contextual data delivery functionality of the system of FIG. 1.

FIG. 14 depicts another embodiment of the present disclosure related to context event data delivery. As has been described throughout, controller 102 communicates with the sensor 103 via the body area network 101. In the example in FIG. 14, the sensor 103 is employed in a health monitoring application wherein the sensor 103 continuously monitors heartbeats in an attempt to look for arrhythmic events, heartbeat irregularities, or some other pertinent event similar to the description with reference to FIG. 12.

The sensing device 806 (FIG. 8) receives regular heartbeats and the sensor logic 804 (FIG. 8) transfers data indicative of the heartbeats 1400, 1401, and so on, to the controller 102. When the sensing device 806 detects an arrhythmic event, the sensor logic 804 transmits data indicative of the arrhythmic event 1402 to the controller 102. In response, the control logic 204 transmits a message 1404 requesting raw data mode.

In response to the request 1404, the sensor logic 804 then transmits raw data 1403 to the controller 102 so that the user can review the actual raw data that is being obtained by the sensing device 806. The sensor logic 804 continues to transmit the raw data 1403 until the control logic 204 transmits a message 1405 requesting that the raw data mode be terminated.

Figure 15:
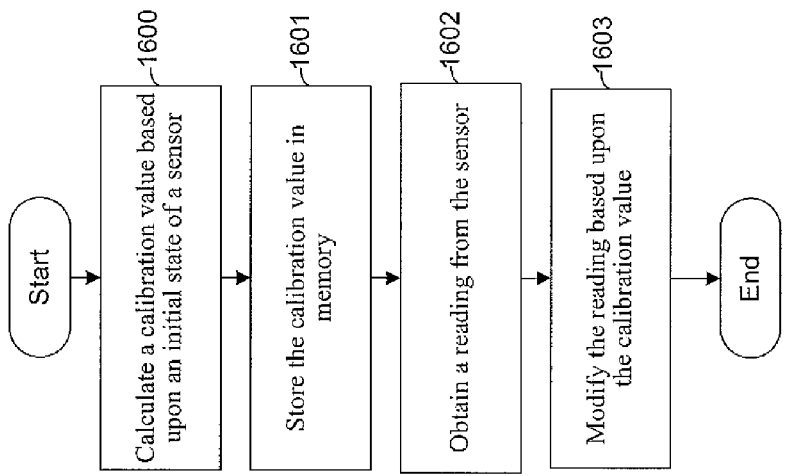
FIG. 15 is a flowchart of exemplary architecture and functionality of the calibration functionality of the sensor logic of the controller of the system of FIG. 1.

FIG. 15 is a flowchart depicting exemplary architecture and functionality of the control logic 204 (FIG. 2) and its calibration functionality. In step 1600, the control logic 204 calculates a calibration value based upon an initial state of a sensor 103-106. In step 1601, the control logic 204 stores the value in memory 201 (FIG. 2).

During operation, the control logic 204 obtains a reading from a sensor 103-106, as indicated in step 1602. In step 1603, the control logic 204 modifies the reading based upon the calibration value.

This invention may be provided in other specific forms and embodiments without departing from the essential characteristics as described herein. The embodiments described above are to be considered in all aspects as illustrative only and not restrictive in any manner.

As described above and shown in the associated drawings, the present invention comprises wireless sensor network and method for using the same. While particular embodiments of the invention have been described, it will be understood, however, that the invention is not limited thereto, since modifications may be made by those skilled in the art, particularly in light of the foregoing teachings. It is, therefore, contemplated by the appended claims to cover any such modifications that incorporate those features or those improvements that embody the spirit and scope of the present invention.

The invention claimed is:

1. A system, comprising:
   at least one sensor for measuring acceleration coupled to a body of a user, the sensor having an axis system that is offset from an axis system of the user based upon placement of the sensor on the body of the user;
   a controller communicatively coupled to the sensor via a network; and
   logic configured to receive a first acceleration measurement in an x-direction of the sensor's axis system and a second acceleration measurement in a z-direction of the sensor's axis system when the user is standing in a vertical position, the logic further configured to calculate a first angle value indicative of a first angular offset value between the user's axis system and the sensor's axis system and a second angle value indicative of a second angular offset value between the user's axis system and the sensor's axis system based upon the first measurement and the second measurement and an assumption that static effects of gravity only affect a z-axis of the sensor in a magnitude of 1 g, the logic further configured to store the first and second angle values in memory.

2. The system of claim 1, wherein the logic is further configured to obtain at least one measurement from the sensor and modify the measurement based upon the angle values.

3. The system of claim 1, wherein an initial state of the sensor is based upon a location of the sensor on a body.

4. The system of claim 1, wherein an initial state of the sensor is based upon a measure of the sensor's performance.

5. The system of claim 1, wherein an initial state of the sensor is based upon a measure of the performance of a battery powering the sensor.

6. The system of claim 1, wherein an initial state of the sensor is based upon a measure of the temperature in an operating environment of the sensor.

7. The system of claim 1, wherein an initial state of the sensor is based upon a measure of the humidity in an operating environment of the sensor.

8. The system of claim 1, wherein the logic is further configured to calculate an effect related to an operation-changing factor and generate a function representing the affect of the factor on the sensor.

9. The system of claim 8, wherein the logic is further configured to receive a third acceleration measurement from the sensor and apply the function to the third acceleration measurement.

10. A method, comprising the steps of:
coupling a sensor for measuring acceleration to a user's body, the sensor having an axis system that is offset from an axis system of the user based upon placement of the sensor on the on the body of the user;
communicatively coupling a controller to the sensor;
receiving a first acceleration measurement from the sensor in an x direction of the sensor's axis system when the user is standing in a vertical position;
receiving a second acceleration measurement from the sensor in a z-direction of the sensor's axis system when the user is standing in the vertical position;
calculating a first angle value indicative of a first angular offset value between the user's axis system and the sensor's axis system and a second angle value indicative of a second angular offset value between the user's axis system and the sensor's axis system based upon the first acceleration measurement and the second acceleration measurement and an assumption that static effects of gravity only affect a z-axis of the sensor in a magnitude of 1 g; and
storing the first and second angle values in memory.

11. The method of claim 10, further comprising the step of modifying a third acceleration measurement based upon the first and second angle values.

12. The method of claim 10, wherein the calculating step further comprises the step of calculating an initial state of the sensor based upon a location of the sensor on the body.

13. The system of claim 10, wherein the calculating step further comprises the step of calculating an initial state of the sensor based upon a measure of the sensor's performance.

14. The method of claim 10, wherein the calculating step further comprises the step of calculating an initial state of the sensor based upon a measure of the performance of a battery powering the sensor.

15. The method of claim 10, wherein the calculating step further comprises the step of calculating an initial state of the sensor based upon a measure of the temperature in an operating environment of the sensor.

16. The method of claim 10, wherein the calculating step further comprises the step of calculating an initial state of the sensor based upon a measure of the humidity in an operating environment of the sensor.

17. The method of claim 10, further comprising the step of calculating an effect related to an operation-changing factor and generating a function representing the effect of the factor on the sensor.

18. The method of claim 17, further comprising the steps of:
receiving a measurement from the sensor; and
applying the function to the measurement.

19. A system, comprising:
at least one sensor for measuring acceleration coupled to a body of a user, the sensor having an axis system that is offset from an axis system of the user based upon placement of the sensor on the body of the user;
a controller communicatively coupled to the sensor; and
means for receiving a first acceleration measurement in an x-direction of the sensor's axis system and a second acceleration measurement in a z-direction of the sensor's axis system when the user is standing in a vertical position; and
means for calculating a first angle value indicative of a first angular offset value between the user's axis system and the sensor's axis system and a second angle value indicative of a second angular offset value between the user's axis system and the sensor's axis system based upon the first acceleration measurement, the second acceleration measurement, and an assumption that the static effects of gravity only affect a z-axis of the sensor in a magnitude of 1 g.

* * * * *